United States Patent
Chuang et al.

(10) Patent No.: US 9,958,424 B2
(45) Date of Patent: May 1, 2018

(54) METHOD OF IDENTIFYING AIRBORNE MOLECULAR CONTAMINATION SOURCE

(71) Applicant: TAIWAN SEMICONDUCTOR MANUFACTURING COMPANY, LTD., Hsin-Chu (TW)

(72) Inventors: Tzu-Sou Chuang, Hsinchu (TW); Jeng-Jyi Hwang, Chu-Tong Town, Hsinchu County (TW); Cheng-Lung Chou, Chu-Tong Town, Hsinchu County (TW); Chi-Ming Yang, Hsinchu (TW); Chin-Hsiang Lin, Hsin-Chu (TW)

(73) Assignee: TAIWAN SEMICONDUCTOR MANUFACTURING COMPANY, LTD., Hsin-Chu (TW)

( * ) Notice: Subject to any disclaimer, the term of this patent is extended or adjusted under 35 U.S.C. 154(b) by 1052 days.

(21) Appl. No.: 13/632,530

(22) Filed: Oct. 1, 2012

(65) Prior Publication Data
US 2014/0095083 A1    Apr. 3, 2014

(51) Int. Cl.
*G01N 33/00* (2006.01)
*G06F 15/00* (2006.01)

(52) U.S. Cl.
CPC ......... *G01N 33/0004* (2013.01); *G06F 15/00* (2013.01)

(58) Field of Classification Search
None
See application file for complete search history.

(56) References Cited

U.S. PATENT DOCUMENTS

| | | | |
|---|---|---|---|
| 2003/0020928 | A1 | 1/2003 | Ritzdorf et al. |
| 2009/0317214 | A1* | 12/2009 | Hsiao et al. ............... 414/217 |
| 2011/0232771 | A1 | 9/2011 | Lenz |
| 2011/0233198 | A1 | 9/2011 | Okuno et al. |
| 2012/0078417 | A1 | 3/2012 | Connell, II et al. |

FOREIGN PATENT DOCUMENTS

| | | |
|---|---|---|
| KR | 1020100028293 | 3/2010 |
| KR | 1020100046328 | 5/2010 |

OTHER PUBLICATIONS

Liu et al., "Location identification for indoor instantaneous point contaminant source by probability-based inverse computational fluid dynamics modeling" (Indoor Air, 2008).*

(Continued)

*Primary Examiner* — An Do
*Assistant Examiner* — Renee I Wilson
(74) *Attorney, Agent, or Firm* — Haynes and Boone, LLP (57) ABSTRACT

The present disclosure provides a method of identifying an airborne molecular contamination (AMC) leaking source in a fab. The method includes distributing a sensor in the fab, executing a forward computational fluid dynamics (CFD) simulation of an air flow in the fab, setting an inversed modeling of the forward CFD simulation of the air flow in the fab, building up a database of a spatial response probability distribution matrix of the sensor using an AMC measurement data in the fab, and identifying the AMC leaking source using the database of the spatial response probability distribution matrix of the sensor.

20 Claims, 13 Drawing Sheets

(56) References Cited

OTHER PUBLICATIONS

Hu et al., "Deterministic simulation and assessment of air-recirculation performance of unidirectional-flow cleanrooms that incorporate age of air concept" (Building and Environment 2003).*

Kwang-Chul Noh et al., "Analysis on the Airflow and the Gas Contamination Characteristics in Super Clean Room," Collected Papers of Summer Academic Conference of the Society of Air-Conditioning and Refrigerating Engineers of Korea (2003), pp. 1117-1122, Korea (2003).

Korean Intellectual Property Office, "Notice of Allowance of Patent," dated Oct. 21, 2014, for Application No. 10-2013-0015753, 3 pages, Korea.

S.C. Hu et al., "Deterministic Simulation and Assessment of Air-Recirculation Performance of Unidirectional-Flow Cleanrooms that Incorporate Age of Air Concept," Building and Environment 38 (2003), pp. 563-570, Taipei.

James, J.J. Hwang et al., "Innovative Approach to Identify Location of AMC Source in Cleanroom by Inverse Computational Fluid Dynamics Modeling", IEEE, May 15-17, 2012, Saratoga Springs, NY, 6 pages.

Office Action issued in German Application No. 10 2013 103 696.1 dated Jun. 6, 2016.

* cited by examiner

METHOD OF IDENTIFYING AIRBORNE MOLECULAR CONTAMINATION SOURCE

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process) has decreased. This scaling down process generally provides benefits by increasing production efficiency and lowering associated costs. Such scaling down has also increased the complexity of processing and manufacturing ICs and, for these advances to be realized, similar developments in IC processing and manufacturing are needed.

For example, airborne molecular contamination (AMC) becomes a more and more serious issue in semiconductor manufacturing process for further scaling down the geometry size. If an AMC sensor reaches or exceeds an allowed AMC concentration level in a fab, a common procedure for identifying the AMC leakage source and location utilizes significant human time and resources. The procedure is also slow for identifying the AMC leaking source and location. That may adversely affect the semiconductor manufacturing process, the fab and associated IC devices. Accordingly, what is needed is a method to identify the AMC leaking source and location in a quick way if the AMC sensor is alarmed.

BRIEF DESCRIPTION OF THE DRAWINGS

The present disclosure is best understood from the following detailed description when read with accompanying figures. It is emphasized that, in accordance with the standard practice in the industry, various features are not drawn to scale and are used for illustration purpose only. In fact, the dimension of the various features may be arbitrarily increased or reduced for clarity of discussion.

DETAILED DESCRIPTION

The following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Figure 1:
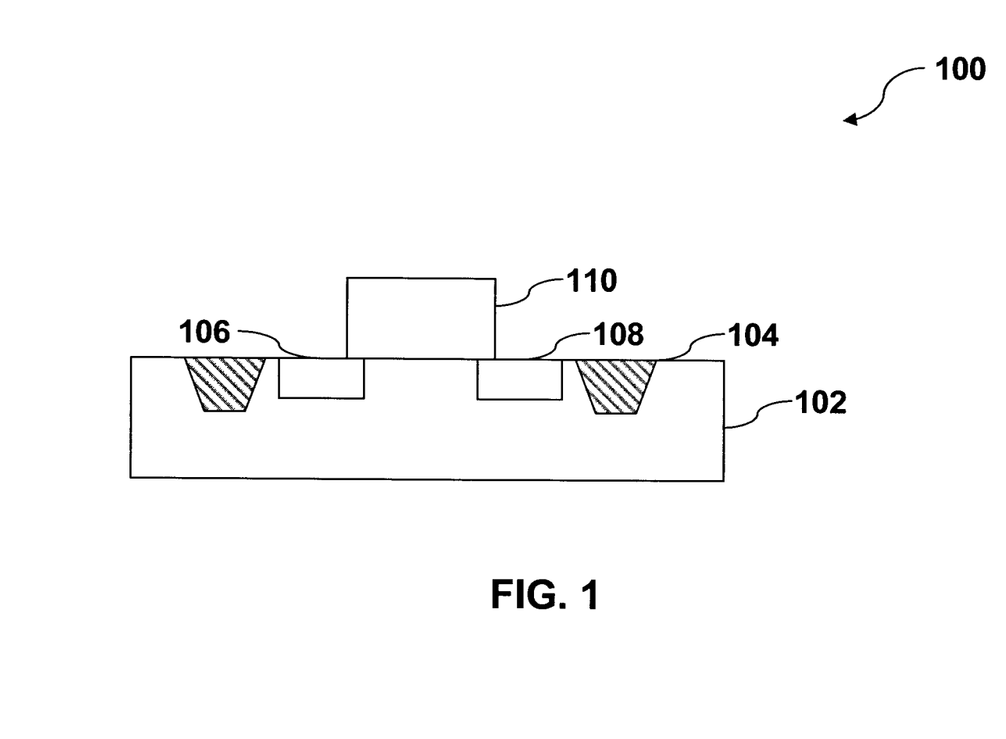
FIG. 1 represents a cross-sectional side view of a device according to one or more embodiments of the present disclosure.

Referring now to FIG. 1, a cross-sectional side view of a device 100 formed in a fab is illustrated according to one or more embodiments of the present disclosure. The device 100 includes a substrate 102, an isolation feature 104, a source 106, a drain 108, and a gate stack 110. However, other configurations and inclusion or omission of devices may be possible. In some embodiments, the substrate 102 includes a wafer and/or a plurality of conductive and non-conductive thin films. The wafer is a semiconductor substrate including silicon (in other words, a silicon wafer). Alternatively or additionally, the wafer includes another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP. In yet another alternative, the wafer is a semiconductor on insulator (SOI). The plurality of conductive and non-conductive thin films may comprise an insulator or a conductive material. For example, the conductive material comprises a metal such as aluminum (Al), copper (Cu), tungsten (W), nickel (Ni), titanium (Ti), gold (Au), and platinum (Pt) and, thereof an alloy of the metals. The insulator material may include silicon oxide and silicon nitride. The substrate 102 further includes various doped features, such as n-type wells and/or p-type wells, formed by ion implantation or diffusion.

The isolation feature 104 is formed in the substrate 102. Various processes, for example, film deposition, photo lithography, etching, chemical mechanical polishing (CMP), and cleaning, are involved to form the isolation feature 104. The source 106 and the drain 108 are formed in the substrate 102. The source 104 and the drain 106 include an n-type dopant or a p-type dopant, formed by ion implantation or other suitable process. For example, the source 104 and the drain 106 are formed in a common ion implantation procedure. The gate stack 110 is formed by a process including depositing or growing to form multiple layer of films on the substrate 102, patterning a resist film deposited on the substrate 102, and etching the patterned resist film to form the gate stack.

Continuing with the present embodiment, the device 100 is fabricated in the fab. Pluralities of chemicals are used to form the device 100 in various processes. A fab environment must be well controlled to guarantee quality of the device 100. Any chemical leak or airborne molecular contamination (AMC) in the fab can have a devastating impact on the device 100. The AMC impacts include a photo resist T-topping, uncontrolled boron or phosphorus doping, etching rate shift, adhesion failure, corrosion on metal line, hazing on mask (or reticle) or optics of an exposing tool, and electrical parameter shift, such as threshold voltage shift, resistivity shift, and high contact resistance.

Figure 2:
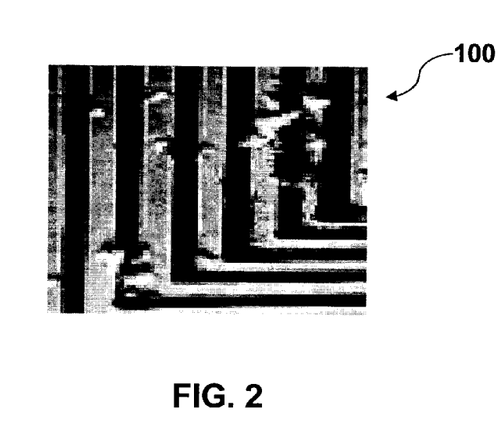
FIGS. 2-5 represent examples of airborne molecular contamination (AMC) impact on a device according to one or more embodiments of the present disclosure.
Figure 3:
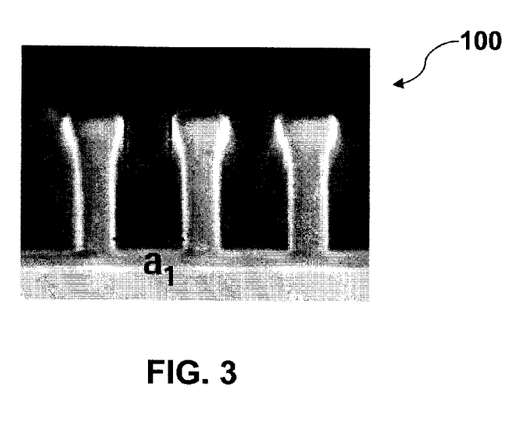
Figure 4:
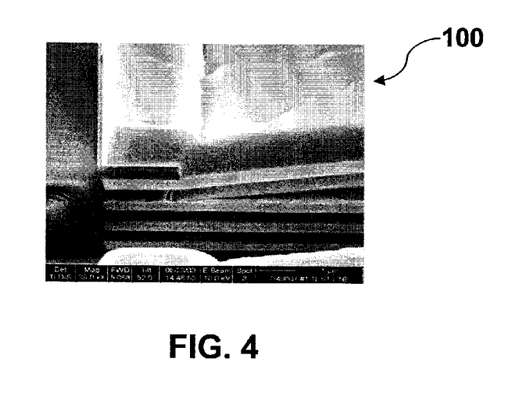
Figure 5:
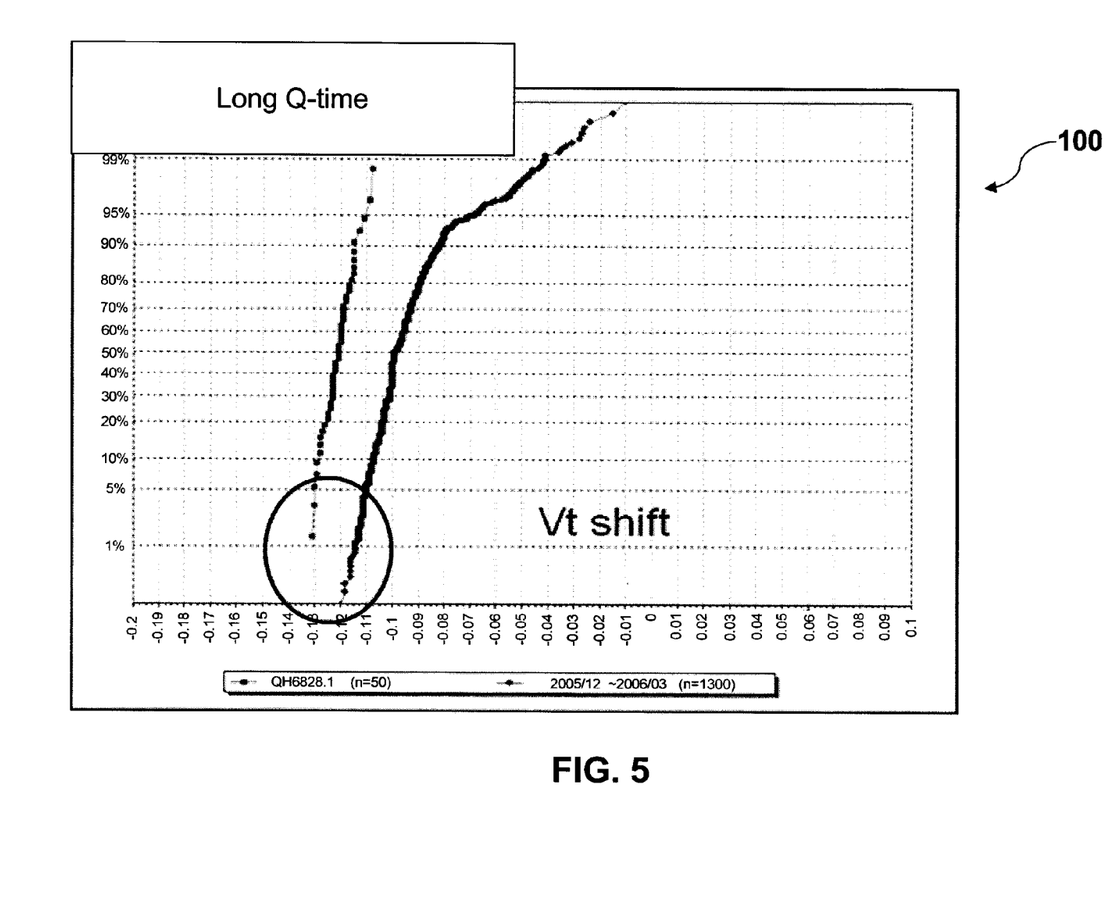

Referring now to FIGS. 2-5, examples of airborne molecular contamination (AMC) impact on the device 100 are illustrated according to one or more embodiments of the present disclosure. In some embodiments, the AMC includes four types (A, B, C, and D) of contamination source. Type A represents an acid corrosive material, such as HF, HCl, $H_2SO_4$, or $HNO_3$. FIG. 2 is an example of the acid causing the corrosion on a metal line of the device 100. Type B represents a base corrosive material, such as ammonia ($NH_3$), amine, or N-Methyl-2-pyrrolidone (NMP). The base can neutralize the acid generated by a photo-induced chemical amplified reaction (CAR) in a deep ultraviolet (DUV) photo resist and may form a T-topping of a photo resist profile as shown in FIG. 3. Type C represents a condensable or an organic material, such as dioctyl phthalate (DOP), butylated hydroxyl toluene (BHT), siloxanes, or isopropyl alcohol (IPA). Type C material may cause mask (or reticle) haze, or adhesion failure of the IC device. FIG. 4 is an example of the adhesion failure of the IC device caused by type C contamination. Type D represents a dopant material, such as $BF_3$, triethyl phosphate (TEP), trimethyl phosphate (TMP) or triethyoxyphosphine oxide (TEPO). Type D contamination may cause electrical parameter shift, for example, a $V_T$ (threshold voltage) shift as shown in FIG. 5.

Figure 6:
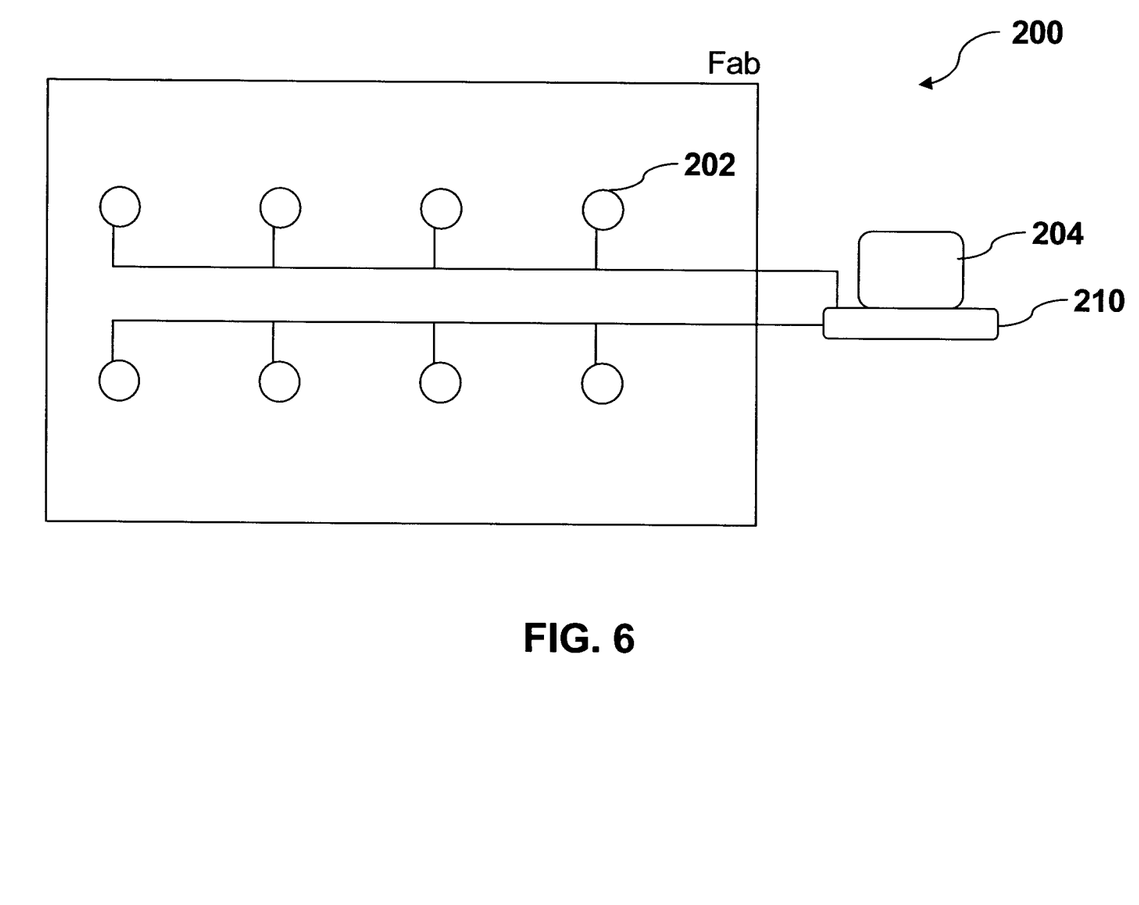
FIG. 6 is a diagram of an AMC monitoring system monitoring the AMC concentration level during fabricating a device in a fab according to one or more embodiments of the present disclosure.

Referring now to FIG. 6, an example of an AMC monitoring system 200 is provided for monitoring the AMC contamination during fabricating of the device 100 according to one or more embodiments of the present disclosure. The AMC monitoring system 200 includes an AMC plurality of sensors 202, an AMC monitor 204. The AMC sensors 202 are distributed inside the fab and connected to the AMC monitor 204. The AMC monitor 204 includes an alarm. The AMC monitoring system 200 also includes a computer 210 with a processor and memory for executing instruction, and can be used to implement some or all of the method below. The AMC sensors 202 are configured to detect an AMC concentration level in the environment of the fab.

Figure 7:
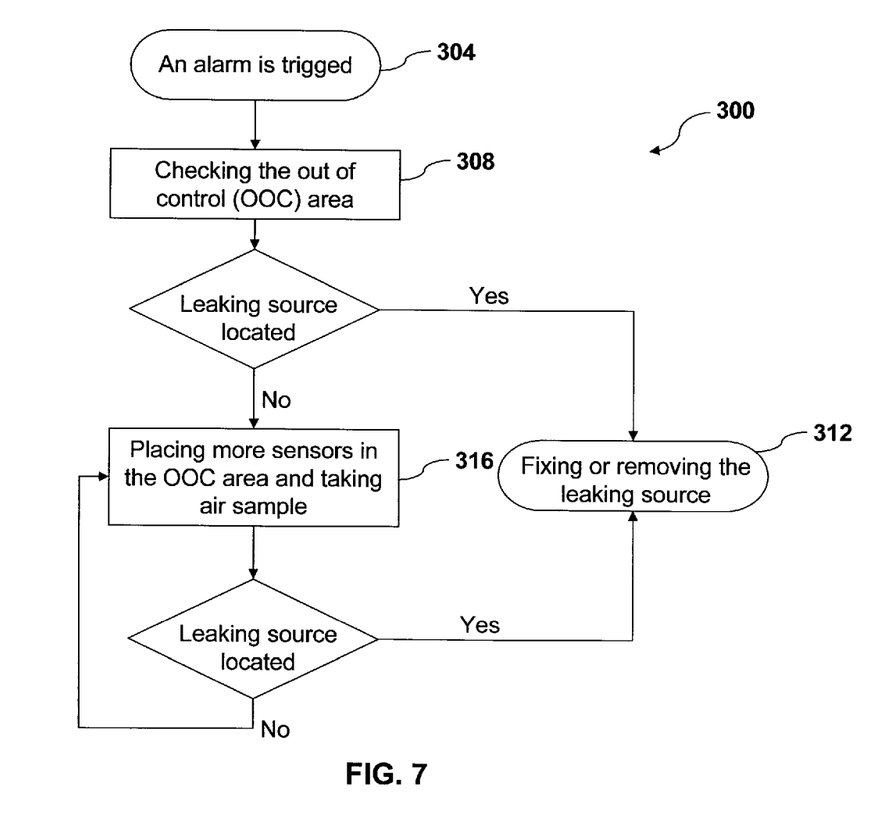
FIG. 7 is a flow chart of a method identifying an AMC leaking source or location in a fab according to one or more embodiments of the present disclosure.

Referring now to FIG. 7, a flow chart of a method 300 for identifying an AMC leaking source or location in the fab is illustrated according to one or more embodiments of the present disclosure. In the present embodiments, when the concentration level of the AMC in the fab reaches or exceeds an allowed concentration level or out of control (OOC) for fabricating the IC device in the fab, the alarm is trigged at step 304. The method 300 proceeds to step 308 for checking the nearby area of the AMC sensor 202 trigging the alarm of the AMC monitor 204. If an AMC leaking source is located, the method 300 proceeds to step 312 for fixing the AMC leaking source or removing the AMC leaking source from the fab. If the leaking source is not located, the method 300 proceeds to step 316 for placing more AMC sensors 202 in the OOC area and nearby area and adjusting some of the sensors 202 with wide range. An air sample may be taken and sent to a chemical lab for analysis to help identify the AMC leaking source or location. If an AMC leaking source is located, the method 300 proceeds to step 312 for fixing the AMC leaking source or removing the AMC leaking source from the fab. If the leaking source is not located, the method 300 will repeat at step 316 until the AMC leaking source is located and fixed or removed from the fab. Additional steps can be provided before, during, and after the method 300, and some the steps described can be replaced, eliminated, or moved around for additional embodiments of the method 300. The method 300 identifying the AMC leaking source and location is time and resource consuming. Therefore, the response to the AMC leaking is slow.

Figure 8:
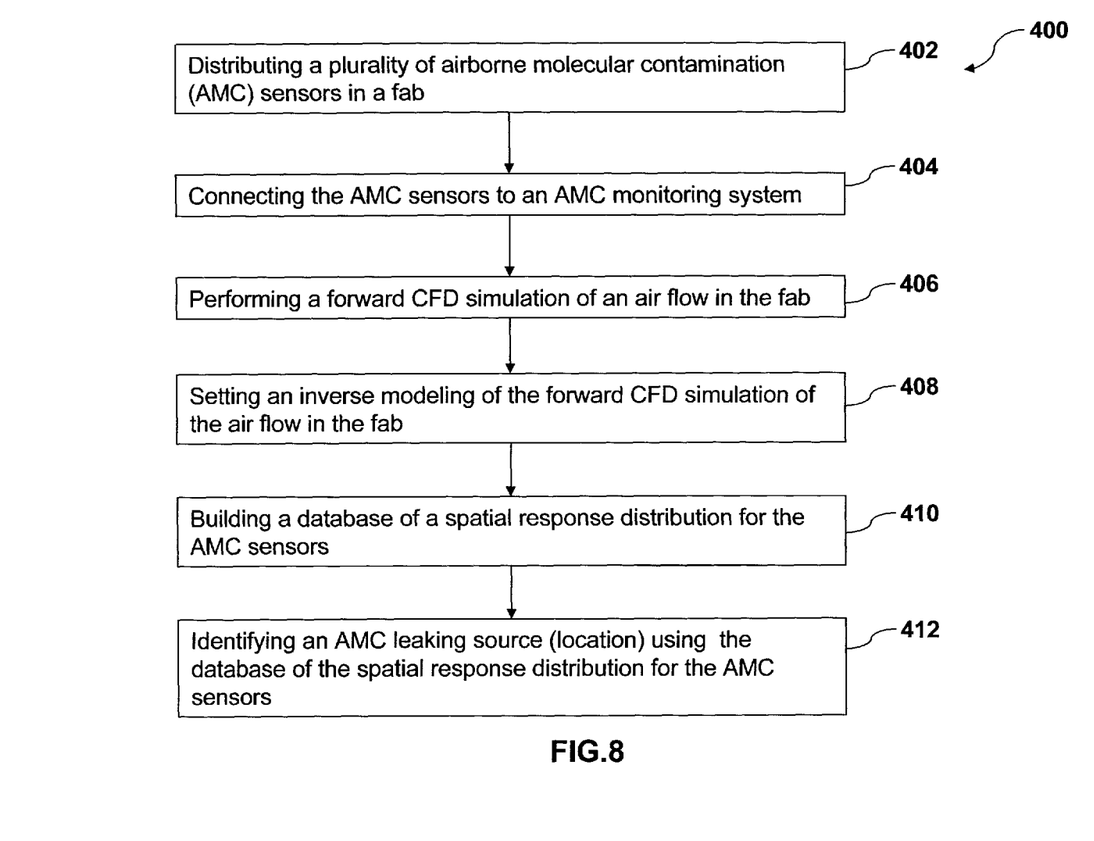
FIG. 8 is a flow chart of a method identifying the AMC leaking source or location in a fab for implementing one or more embodiments of the present disclosure.

Referring now to FIG. 8, a flow chart of a method 400 identifying the AMC leaking source or location in the fab is illustrated for implementing one or more embodiments of the present disclosure. The method 400 begins at step 402 by distributing a plurality of the AMC sensors in the fab. In the present embodiments, an AMC sensor is also referred to as a sensor. The AMC sensors can detect one or more of the four types of the AMC chemicals (type A, B, C or D) in the fab. The method 400 proceeds to step 404 for connecting the AMC sensors to a AMC monitoring system discussed below with reference to FIG. 6. The method 400 proceeds to step 406 for performing a forward CFD simulation of an air flow in the fab. The step 406 includes providing an air flow streamline in the fab. The step 406 also includes determining and optimizing a layout of the AMC sensors in the fab. The optimized layout of the AMC sensors in the fab will provide required measurement data for the AMC leaking source tracking in the fab with the least amount of the AMC sensors. The method 400 proceeds to step 408 for setting an inverse modeling of the forward CFD simulation of the air flow in the fab. The step 408 includes providing an inversed air flow streamline in the fab. The method 400 proceeds to step 410 for building a database of a spatial response distribution for the AMC sensors. The step 420 includes calculating a spatial probability distribution matrix for each AMC sensor using the inversed air flow streamlines in the fab. The method 400 proceeds to step 412 for identifying an AMC leaking source or location if one or more AMC sensors reach the OOC level. The step 412 includes identifying the AMC leaking source (location) using the database of the spatial response distribution for the AMC sensors. The step 412 further includes fixing or removing the AMC leaking source. Additional steps can be provided before, during, and after the method 400, and some the steps described can be replaced, eliminated, or moved around for additional embodiments of the method 400.

Figure 9:
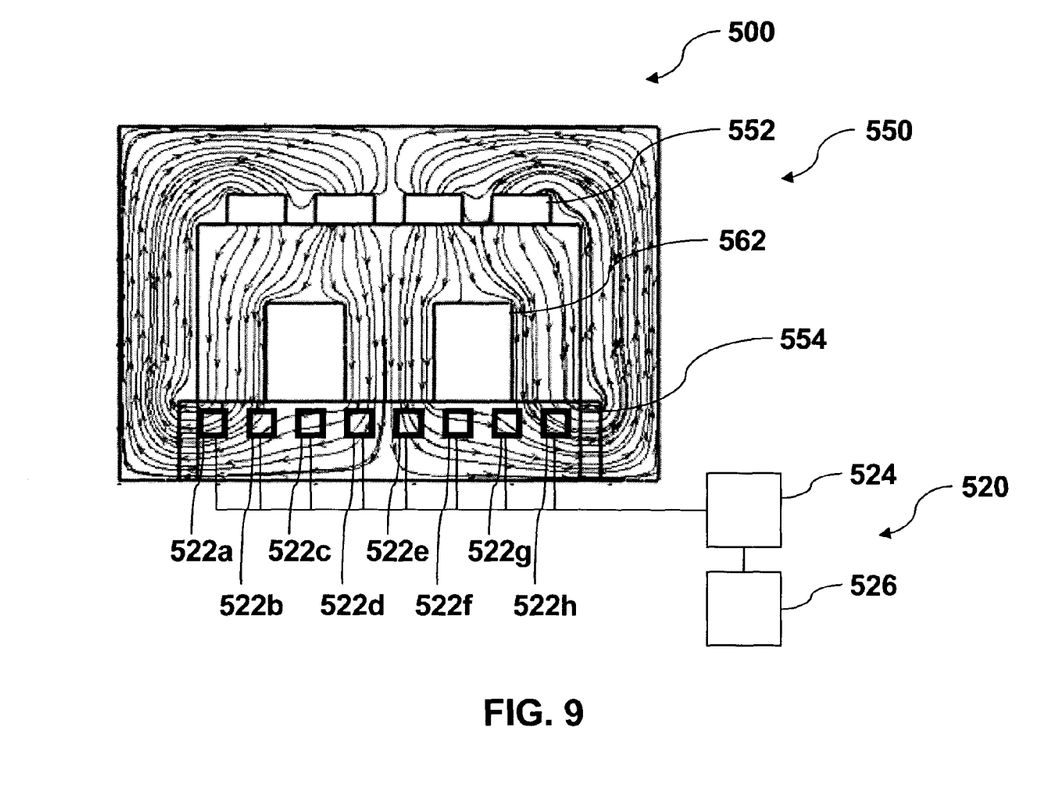
FIG. 9 illustrates a sectional view of a forward air flow streamline simulated by computational fluid dynamics calculation in a fab according to one or more embodiments of the present disclosure.

Referring now to FIG. 9, a cross sectional view of a forward air flow streamline 500 simulated by an CFD in a fab 550 is illustrated according to one or more embodiments of the present disclosure. The AMC monitoring system 520 is designed to monitor the AMC level of the fab 550. The AMC monitoring system 520 includes AMC sensors 522a-h, a AMC controller 524, and data storage 526. However, other configurations and inclusion or omission of the system 520 may be possible. The AMC sensors 522a-h are connect the AMC controller 524. The AMC sensors 522a-h can detect the AMC concentration level in the fab 550. When the AMC concentration level reaches or exceeds to the allowed limit or out of control (OOC) for fabricating the IC device in the fab 550, the alarm signal will trigger the controller to identify the AMC leaking source. The AMC controller 524 includes a computer running the data processing. The AMC controller 524 is also connected with the data storage 526.

As shown in FIG. 9, the fab 550 includes a fan filter unit (FFU) 552, a perforated floor 554, and a process tool 562. However, other configurations and inclusion or omission of the fab 550 may be possible. The FFU 552 includes an inlet and an outlet. The FFU 552 provides continuous and steady clean air to the fab 550. The perforated floor 554 helps to reduce the air flow turbulence in the fab 550 and therefore reduce the number of particles in the fab 550. The process tool 562 may include process tool for fabricating the IC device, for example, a chemical vapor deposition (CVD) tool, a physical vapor deposition (PVD) tool, a resist coating (developing) tool, an expose tool, an etching tool, an implantation tool, a diffusion tool, a chemical mechanical polishing (CMP) tool, or a cleaning tool. In one embodiment, the process tool 562 may also include a measurement tool, such as a film thickness measurement tool, a critical dimension (CD) measurement tool, or a stepper height measurement tool. In another embodiment, the process tool 562 also includes a chemical storage tank storing a chemical, for example, storing the acid, base, photo resist, chemical solvent, or dopant. The process tool 562 may be the source of the AMC leaking.

As shown in FIG. 9, the forward air flow streamline 500 is simulated by the CFD. The arrow indicates the air flow direction. The clean air is provide to the fab 550 through the outlet of the FFU 552, the clean air flows from top of the fab 550 to bottom of the fab, and the clean air is sent to the inlet of the FFU 552 for recycle use.

The forward contaminant transport equation is presented as below $$\frac{\partial C}{\partial t} + U_j \frac{\partial C}{\partial x_j} = \frac{\partial}{\partial x_j}\left(v \frac{\partial C}{\partial x_j}\right) + M_s \cdot \delta(\bar{x} - \bar{x}_{source}) \cdot \delta(t) \quad \text{Eq. (1)}$$

$$\delta(x) = \begin{cases} 1 & x = 0 \\ 0 & x \neq 0 \end{cases}$$

Where, C is the species concentration, $U_j$ is the air velocity at $x_j$ direction, $M_s$ is contamination source mass, $x_{source}$ ($x_s$) is the source location. With partial derivative of the Eq. (1) with respect to $M_s$, Eq. (2) is obtained as following $$\frac{\partial \psi}{\partial t} + U_j \frac{\partial \psi}{\partial x_j} = \frac{\partial}{\partial x_j}\left(v \frac{\partial \psi}{\partial x_j}\right) + \delta(\bar{x} - \bar{x}_{source}) \cdot \delta(t) \quad \text{Eq. (2)}$$

$$\psi = \frac{\partial C}{\partial M_s}$$

$$\psi|_{t=0} = 0$$

Where $\psi = \psi$ (x; t=T, $x_s$) is the state sensitivity of resident concentration at x to the source $M_s$ at $x_s$. Eq. (3) is obtained as below following the derivation of adjoint equation, $$\frac{\partial \psi^*}{\partial \tau} - U_j \frac{\partial \psi^*}{\partial x_j} = \frac{\partial}{\partial x_j}\left(v \frac{\partial \psi^*}{\partial x_j}\right) + \delta(\bar{x} - \bar{x}_{source}) \cdot \delta(\tau) \quad \text{Eq. (3)}$$

$$\delta(x) = \begin{cases} 1 & x = 0 \\ 0 & x \neq 0 \end{cases}$$

$$\tau = T_{obs} - t$$

with initial condition and boundary conditions.

$$\psi^*|_{t=0} = 0$$

$$\psi^* = 0 \text{ on } \Gamma_1$$

$$U_j \psi^* + v \frac{\partial \psi^*}{\partial xj} = 0 \text{ on } \Gamma_2$$

$$v \frac{\partial \psi^*}{\partial xj} = 0 \text{ on } \Gamma_3$$

Where $\psi^* = \psi^*$ (x; $\tau = T$, $x_o$) is the spatial adjoint probability with respect to the observation location $x_o$. $\tau$ is the backward time. The adjoint probability $\psi^*$ will meet $$\psi^*|_{x=xsource, t=0} = \psi|_{x=xobs, t=T}$$

Figure 10:
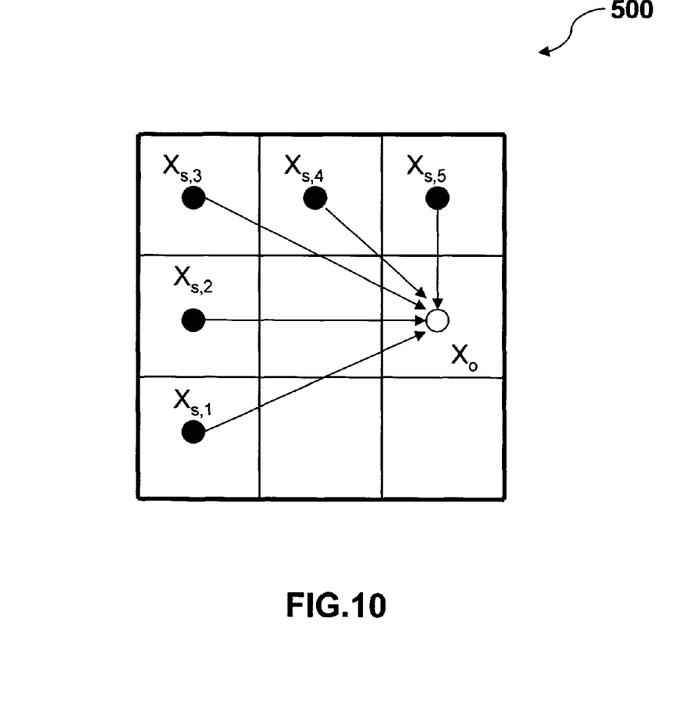
FIGS. 10-11 are example explaining an adjoint equation according to one or more embodiments of the present disclosure.
Figure 11:
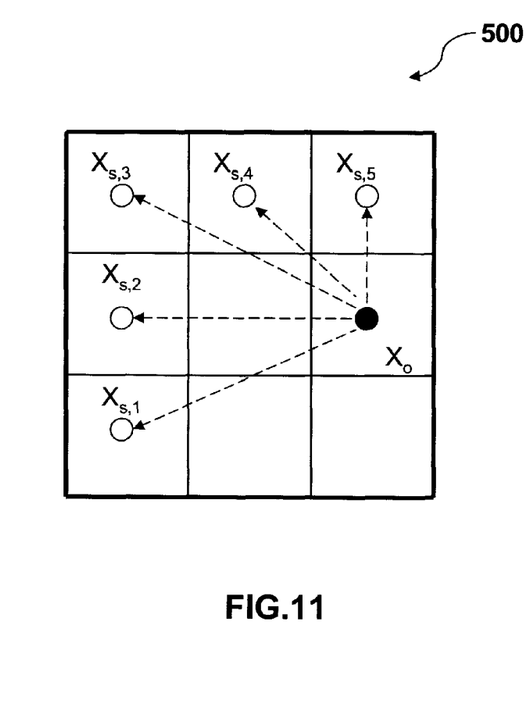

It indicates that the spatial adjoint probability for point S (source) with respect to point O (observation) in adjoint Eq. (3) is the same as the state sensitivity for point O with respect to point S in forward equation (Eq. (2)). The concepts are shown in FIGS. 10-11. It is observed that the flow direction is inversed in the adjoint equation (Eq. (3)).

The Eq. (3) calculates the adjoint probability $\psi^*$ (x; $\tau = T$, $x_o$), the probability of source location based on the observation (sensor) location O. The air flow field is required as input for the simulation. Combination of the CFD and the adjoint equation constitute the mathematical methodology of inversed modeling. Through the methodology, if there are more sensors at $\chi_{oi}$ ($=\chi_{o1}, \chi_{o2}, \ldots \chi_{on}$), the adjoint spatial probability matrices ($\psi^*_1, \psi^*_2, \ldots \psi^*_n$) of the source with respect to the n sensor locations. For multiple sensors $\chi_{oi}$ ($=\chi_{oi}, \ldots \chi_{on}$), detection with reading ($X_1, X_2, \ldots X_n$), and the corresponding adjoint probability matrices of contamination source obtained as $\psi^*_1, \psi^*_2, \ldots \psi^*_n$, the spatial probability distribution $\Phi$ of contamination source is expressed in Eq. (4).

$$\Phi = \sum_{i=1}^{N} X_i \psi * i \Bigg/ \left|\sum_{i=1}^{N} X_i \psi * i\right| \quad \text{Eq. (4)}$$

The $\Phi$ is a 3-dimensional matrix. Its elements represent the probabilities of being the contamination source in the spatial coordinate based on the contamination measurement values from n sensors distributed at locations. From the probability level in the matrix elements, the contamination source location can be identified.

Figure 12:
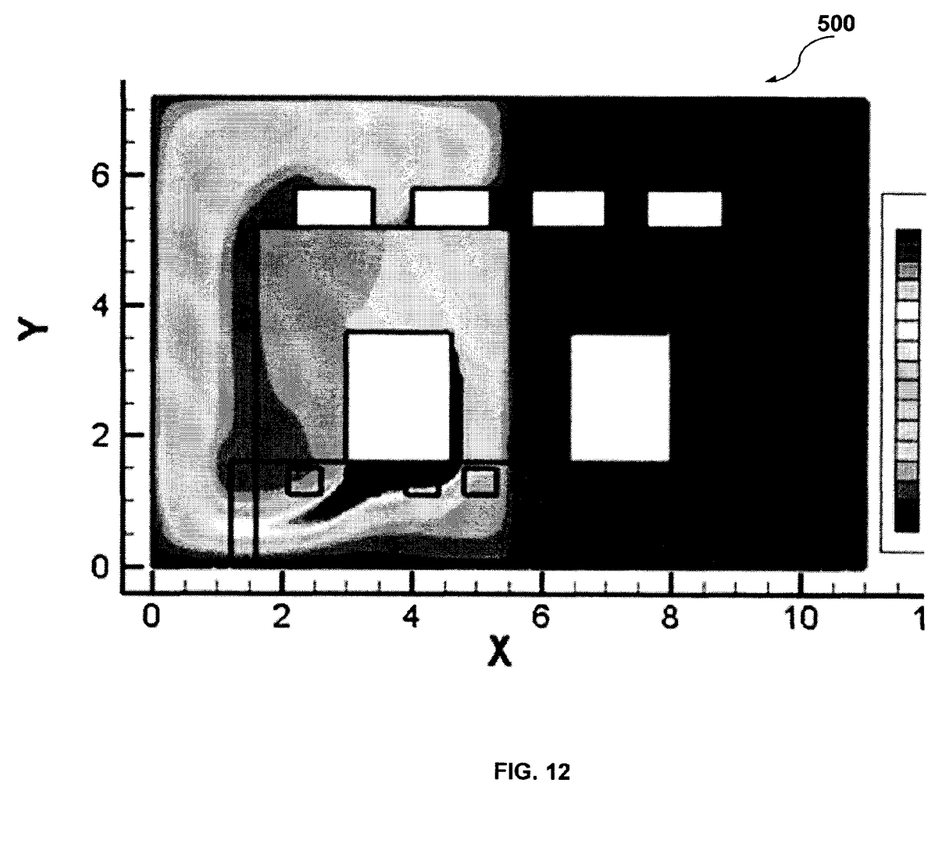
FIG. 12 illustrates a diagram of AMC concentration simulated by computational fluid dynamics (CFD) according to one or more embodiments of the present disclosure.

As shown in FIG. 9, in the AMC monitoring system 520, the distribution of the AMC sensors 522a-h in the fab 550 is very important. The AMC sensors 522a-h is able to detect the AMC concentration in the fab 550 and provide enough measurement data in an economical and effective way. A successful layout of the AMC sensors 522a-h in the fab 550 provides the required measurement data for AMC leaking source tracking at the lowest amount of sensors installed. In order to determine the layout of the AMC sensors 522a-h, the forward CFD simulation with different condition is conducted. In one embodiment, the forward air flow streamline 500 shown in FIG. 9 is a forward CFD simulation result of the AMC dispersing in the air flow. FIG. 12 is the AMC concentration distribution after one cycle of air flow circulation. The AMC sensors 522a-h can read the AMC concentration at eight locations on the fab 550. The eight AMC concentration readings can be used as an input in a reversed modeling of the forward CFD simulation.

Figure 13:
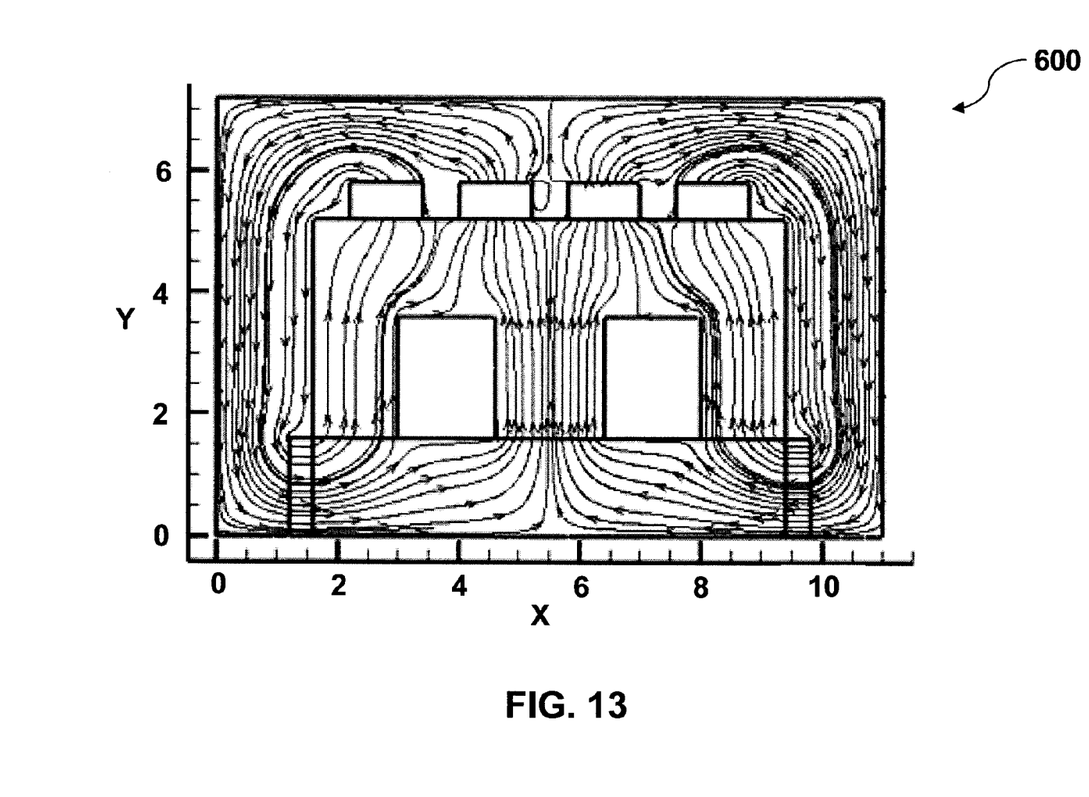
FIG. 13 illustrates a sectional view of an inversed streamline of air flow simulated by inverse modeling of CFD in a fab according to one or more embodiments of the present disclosure.
Figure 14:
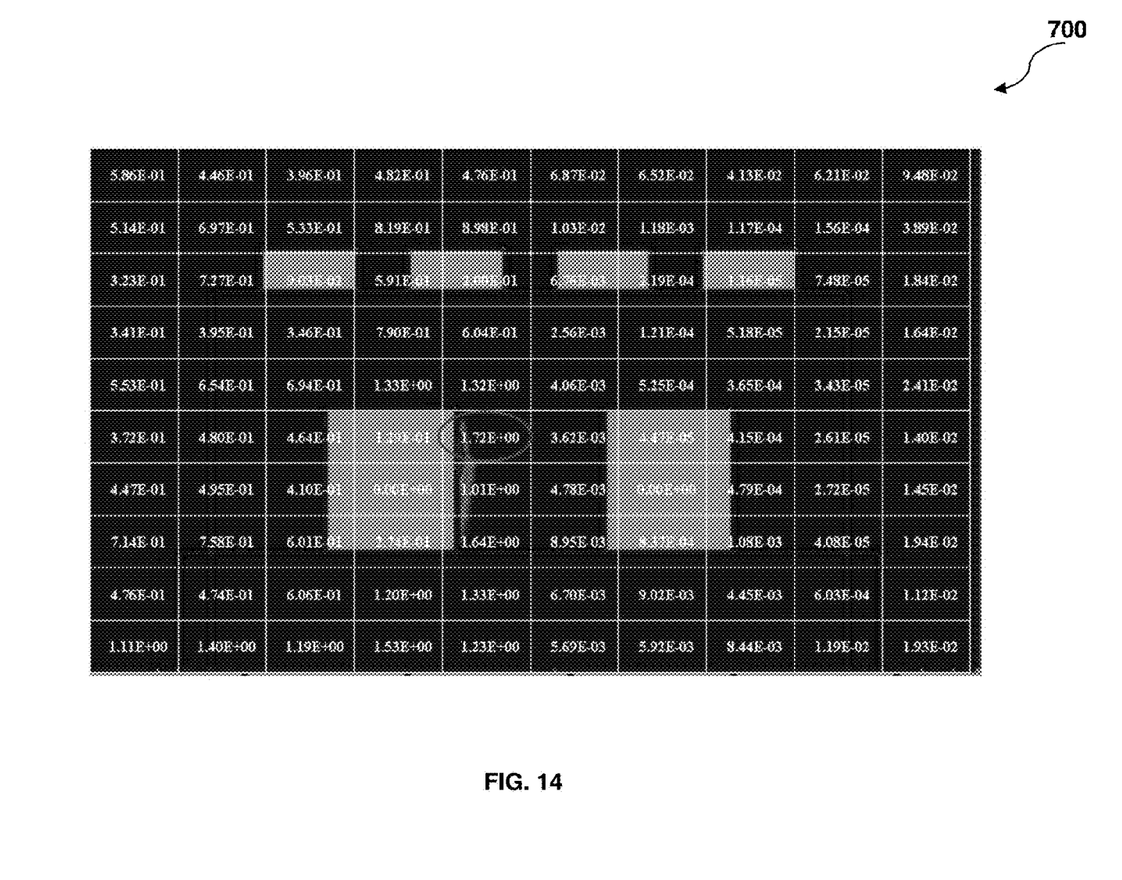
FIGS. 14-16 represent a spatial response probability distribution with respect to an AMC sensor for implementing one or more embodiments in the present disclosure.

Referring now to FIG. 13, a cross sectional view of an inversed air flow streamline 600 simulated by the inverse modeling of CFD in the fab 550 is illustrated for implementing one or more embodiments of the present disclosure. The inversed air flow streamline 600 is calculated by reversing the forward air flow streamline 500 as shown in FIG. 9. In some embodiments, imposing the eight AMC concentration readings from the AMC sensors respectively, eight sets of spatial adjoint probability matrices $\psi^*_1, \psi^*_2 \ldots \psi^*_8$ are obtained. FIG. 14 is an example for the adjoint probability matrices 700 ($\psi^*_2$ with respect to location $\chi_2$) corresponding the AMC sensor 522b. A number in a grid of the adjoint probability metrics 700 as shown in FIG. 14 indicates a probability of the AMC leaking at that grid if the AMC sensor 522b is trigged by the OOC limit. The location imposed in the embodiment as the AMC leaking source does show the highest probability value in FIG. 14.

Figure 15:
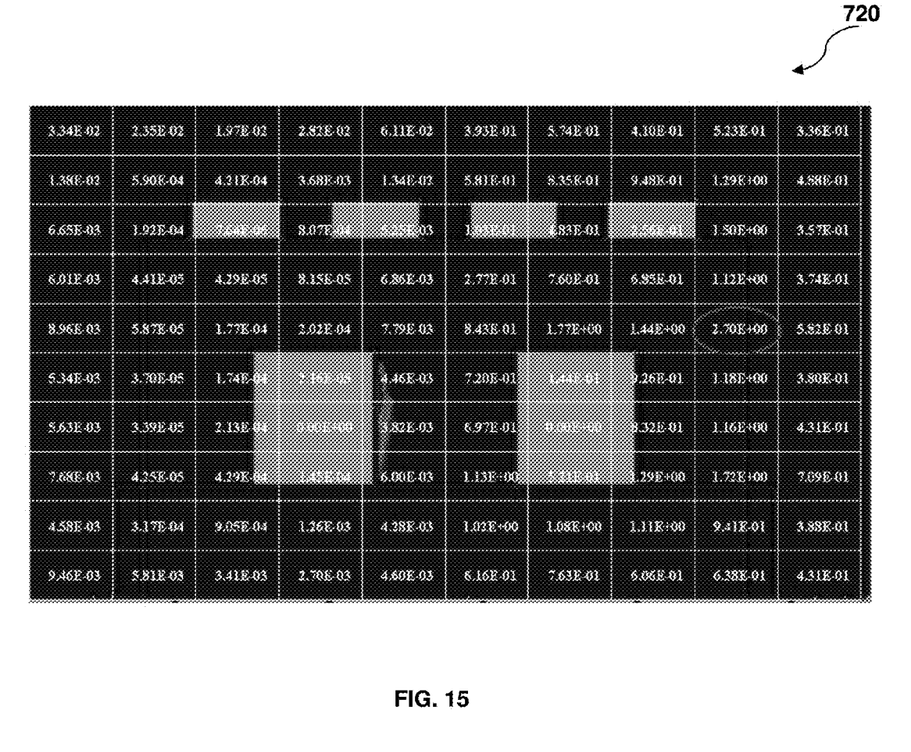

FIG. 15 is another example for the adjoint probability matrices 720 ($\psi^*_8$ with respect to location $\chi_8$) corresponding the AMC sensor 522h. The number in the grid of the adjoint probability metrics 720 as shown in FIG. 15 indicates a probability of the AMC leaking at that grid if the AMC sensor 522h is trigged by the OOC limit. The location imposed in the embodiment as the AMC leaking source does show the highest probability value in FIG. 15.

As shown in FIGS. 14-15, the probability distribution in the adjoint probability metrics 700 or the adjoint probability metrics 720 is sensor location dependent. By using the Eq. (4), the matrices $\psi^*_1, \psi^*_2 \ldots \psi^*_8$ are multiplied with the corresponding reading $X_1, X_2 \ldots X_8$, are summed over the products, and are normalized. A spatial probability matrix of the AMC source location for the fab 550 is generated.

Figure 16:
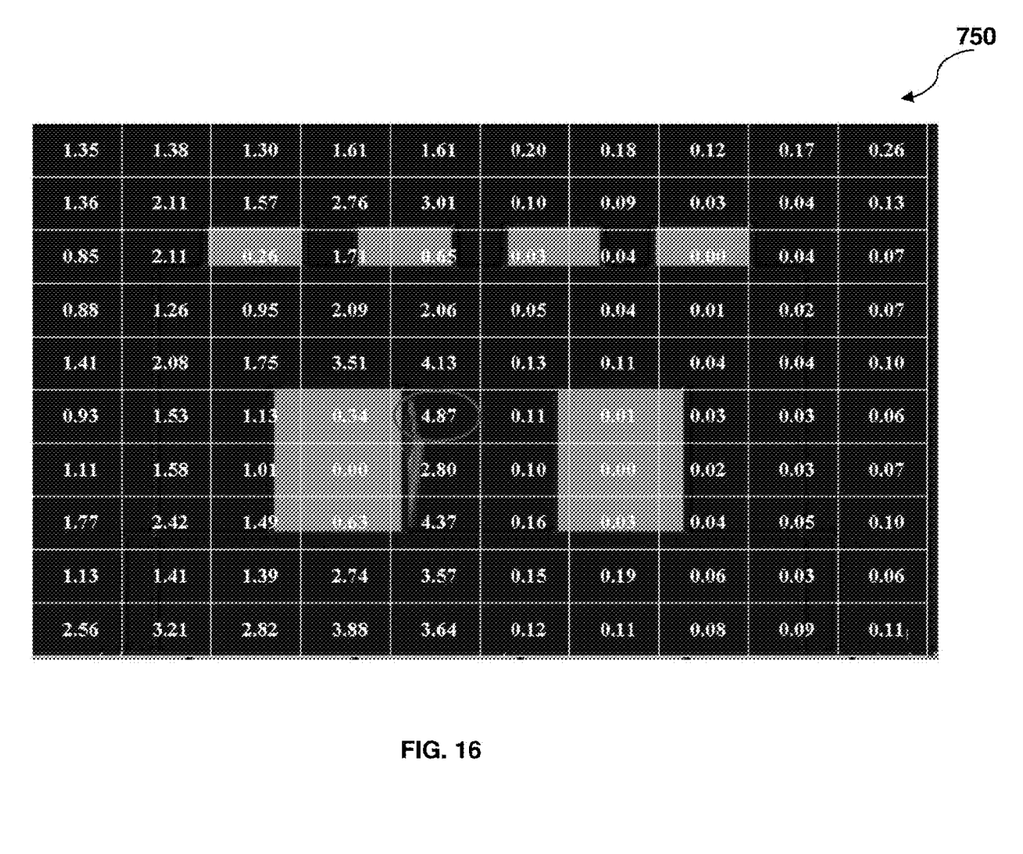

FIG. 16 is an example of a spatial probability matrix 750 of the AMC source location for the fab 550 benefiting from one or more embodiments of the present disclosure. In the present embodiments, a spatial probability matrix is also referred to as a database of a spatial response distribution. When the AMC sensors 522a-h reaches or exceeds the OOC limit, the AMC monitoring system 520 sums over the products of response matrix and corresponding sensor data. The AMC leaking source location is indicated by the spatial probability distribution as shown in FIG. 16. The location imposed in the embodiment as the AMC leaking source does show the highest probability value in FIG. 16.

Thus, the present disclosure described a method of identifying an airborne molecular contamination (AMC) leaking source in a fab. The method includes distributing a sensor in the fab, executing a forward computational fluid dynamics (CFD) simulation of an air flow in the fab, setting an inversed modeling of the forward CFD simulation of the air flow in the fab, building a database of a spatial response probability distribution matrix of the sensor, and identifying the AMC leaking source using the database of the spatial response probability distribution matrix of the sensor. The method further includes connecting the sensor to a CFD controller. The forward CFD simulation of the air flow includes an air flow streamline from an output of a fan filter unit (FFU) to an input of the FFU in the fab. Executing the forward air flow CFD simulation includes optimizing the sensor layout in the fab. Optimizing the sensor layout includes adjusting a number of the sensor in the fab and adjusting position of the sensor in the fab. Setting the inversed modeling of the forward CFD simulation of the air flow includes the air flow streamline from the input of the FFU to the output of the FFU in the fab. Building up the database of the spatial response probability distribution matrix includes setting the spatial response probability matrix of the sensor using an AMC measurement data in the fab. The method further includes adding up the spatial response probability distribution matrix of the sensor. Identifying an AMC leaking source includes locating an AMC source leaking location using the database of the spatial response probability distribution matrix of the sensor.

In some embodiments, a method of identifying an airborne molecular contamination (AMC) leaking source in a fab is presented. The method includes distributing an AMC sensor in the fab, connecting the AMC sensor to a computational fluid dynamics (CFD) system, executing a forward air flow CFD simulation in the fab, performing an inversed forward air flow CFD simulation in the fab, setting a database of a spatial response probability distribution matrix with respect to the AMC sensor, and monitoring the fab using the AMC sensor. Setting the database of the spatial response probability distribution matrix with respect to the AMC sensor includes building the spatial response probability distribution matrix with respect to the AMC sensor by performing the inversed forward air flow CFD simulation in the fab using an unit AMC value with respect to the AMC sensor. The method further includes summing over the products of AMC measurement data and the spatial response probability distribution matrix with respect to the AMC sensor. Monitoring the fab using the AMC sensor includes identifying an AMC leaking source location by searching the database of the spatial response probability distribution matrix with respect to the AMC sensor. The method further includes fixing or removing an AMC leaking source in the fab.

In other embodiments, a setup for identifying an airborne molecular contamination (AMC) leaking source in a fab is also described. The setup includes an AMC controller and a sensor configured to connect the AMC controller. The setup further includes a data storage unit integrated to the AMC controller. The data storage unit is configured to store database of a spatial response probability distribution matrix of the AMC sensor. The AMC controller includes a computer performing the data processing to identify the AMC source, and the database of the spatial response probability distribution matrix of the sensors is stored in data storage. The database of the spatial response probability distribution matrix of the sensors is calculated with inverse modeling of CFD by using an unit AMC value at each AMC sensor location The sensor is designed to monitor the AMC concentration level in the fab so that when the sensor is trigged, the database of the spatial response probability distribution matrix with respect to the sensor is searched and therefore the AMC leaking source is identified.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of identifying an airborne molecular contamination (AMC) leaking source in a fab, the method comprising:

determining a minimum number of AMC sensors needed to collect AMC measurement data for all areas of the fab;

distributing the minimum number of AMC sensors in the fab;

connecting the AMC sensors to an AMC monitor having an alarm;

using a computer, building a database of spatial response probability distribution matrices of the AMC sensors using a unit AMC value at locations of the AMC sensors; and upon a condition that the alarm is triggered by the AMC sensors, collecting AMC measurement data from the AMC sensors, and identifying an AMC leaking source using the AMC measurement data and the database without running a real-time inverse CFD simulation during the collection of AMC measurement data.

2. The method of claim 1, wherein the building of the database includes:

executing a forward computational fluid dynamics (CFD) simulation of an air flow in the fab; and setting an inverse modeling of the forward CFD simulation of the air flow in the fab.

3. The method of claim 2, wherein the forward CFD simulation of the air flow includes an air flow streamline from an output of a fan filter unit (FFU) to an input of the FFU in the fab.

4. The method of claim 3, wherein the setting of the inverse modeling of the forward CFD simulation of the air flow includes streamlining the air flow from the input of the FFU to the output of the FFU in the fab.

5. The method of claim 2, wherein the executing of the CFD simulation includes determining a layout of the AMC sensors in the fab.

6. The method of claim 5, wherein the determining of the layout includes adjusting a number of the AMC sensors in the fab.

7. The method of claim 5, wherein the determining of the layout includes adjusting positions of the AMC sensors in the fab.

8. The method of claim 2, wherein the forward CFD simulation of the air flow includes an air flow streamline around a process tool in the fab.

9. The method of claim 1, wherein the identifying of the AMC leaking source includes:

weighting the spatial response probability distribution matrices of the AMC sensors with the AMC measurement data; and selecting a location of the fab that corresponds to the highest probability value as a result of the weighting.

10. The method of claim 1, further comprising removing the identified AMC leaking source from the fab.

11. The method of claim 1, further comprising storing the collected AMC measurement data in the database.

12. A method of identifying an airborne molecular contamination (AMC) source in a fab, the method comprising:

determining a minimum number of AMC sensors needed to collect AMC measurement data for all areas of the fab;

distributing the minimum number of AMC sensors in the fab;

connecting the AMC sensors to a computational fluid dynamics (CFD) system;

storing a database of spatial response probability distribution matrices with respect to the AMC sensors using the CFD system and a unit AMC value at locations of the AMC sensors; and monitoring the fab using the AMC sensors without running a real-time inverse CFD simulation during the collection of AMC measurement data.

13. The method of claim 12, wherein the storing of the database includes performing an inverse air flow CFD simulation in the fab using the unit AMC value with respect to the AMC sensors.

14. The method of claim 12, wherein the monitoring of the fab includes, upon a condition that an alarm is triggered by the AMC sensors, identifying an AMC leaking source by weighting the database with measurement data from the AMC sensors.

15. The method of claim 14, further comprising fixing or removing the AMC leaking source in the fab.

16. The method of claim 12, wherein the storing of the database includes executing a forward air flow CFD simulation and an inverse air flow CFD simulation in the fab by the CFD system.

17. A system for identifying an airborne molecular contamination (AMC) leaking source in a fab, the system comprising:

an AMC controller;

a number of sensors connected to the AMC controller, the number of sensors being a minimum number of sensors needed to collect AMC measurement data for all areas of the fab; and a storage unit integrated to the AMC controller, wherein the storage unit is configured to store a database of spatial response probability distribution matrices of the sensors derived from a forward computational fluid dynamics (CFD) simulation and an inverse CFD simulation of an air flow in the fab with a unit AMC value at locations of the sensors.

18. The system of claim 17, wherein the AMC controller includes a computer performing AMC source tracking by weighting the spatial response probability distribution matrices of the sensors with AMC data measured by the sensors.

19. The system of claim 17, further comprising an alarm connected to the sensors.

20. The system of claim 17, wherein the fab comprises a fan filter unit (FFU), a perforated floor, and a process tool.

* * * * *